United States Patent [19]
Sunderland et al.

[11] Patent Number: 5,716,729
[45] Date of Patent: Feb. 10, 1998

[54] ELECTROCHEMICAL CELL

[75] Inventors: Walter C. Sunderland, Minnetonka; Anthony W. Rorvick, Brooklyn Park; Donald R. Merritt, Brooklyn Center; Craig L. Schmidt, Eagan; David P. Haas, Brooklyn Park, all of Minn.

[73] Assignee: Medtronic, Inc., Minneapolis, Minn.

[21] Appl. No.: 638,624

[22] Filed: Apr. 26, 1996

[51] Int. Cl.$^6$ .............. H01M 4/00; H01M 6/12; H01M 2/02; H01M 4/02
[52] U.S. Cl. ............ 429/66; 429/162; 429/164; 429/181; 429/211; 429/233; 429/241; 29/623.1
[58] Field of Search .......... 429/66, 162, 164, 429/181, 211, 233, 241; 29/623.1

[56] References Cited

U.S. PATENT DOCUMENTS

| | | | |
|---|---|---|---|
| 3,657,018 | 4/1972 | Rueischi | 136/111 |
| 3,772,083 | 11/1973 | Mead | 136/20 |
| 3,817,790 | 6/1974 | Mitoff | 136/83 |
| 3,826,687 | 7/1974 | Dey | 136/133 |
| 3,829,330 | 8/1974 | Dey | 136/6 LN |
| 3,915,742 | 10/1975 | Battles et al. | 136/6 LF |
| 3,945,850 | 3/1976 | Lewis | 136/107 |
| 4,048,389 | 9/1977 | Bubnick et al. | 429/101 |
| 4,060,671 | 11/1977 | VanderVelden | 429/174 |
| 4,064,329 | 12/1977 | Naylor | 429/174 |
| 4,128,703 | 12/1978 | Mead et al. | 429/101 |
| 4,137,375 | 1/1979 | Coueille | 429/66 |
| 4,224,387 | 9/1980 | Nakayama | 429/133 |
| 4,315,061 | 2/1982 | Ikeda et al. | 429/161 |
| 4,324,847 | 4/1982 | Atheam | 429/181 |
| 4,500,614 | 2/1985 | Nagamine et al. | 429/206 |
| 4,542,080 | 9/1985 | Phillips et al. | 429/174 |
| 4,609,598 | 9/1986 | Tucholski et al. | 429/174 |
| 4,672,010 | 6/1987 | Tucholski et al. | 429/174 |
| 4,824,745 | 4/1989 | Ogawa et al. | 429/213 |
| 5,108,852 | 4/1992 | Tomantschger et al. | 429/66 |
| 5,434,017 | 7/1995 | Berkowitz et al. | 429/94 |

FOREIGN PATENT DOCUMENTS

| | | |
|---|---|---|
| 548816 | 11/1957 | Canada . |
| 58-188050 | 11/1983 | Japan . |

*Primary Examiner*—Kathryn L. Gorgos
*Assistant Examiner*—Edna Wong
*Attorney, Agent, or Firm*—Thomas F. Woods; Harold R. Patton

[57] ABSTRACT

An electrochemical cell has a cathode material formed into a pellet shape which expands as the cell is discharged. A cathode current collector circumferentially surrounds the cathode pellet and is in contact with the peripheral edge of the cathode pellet to prevent peripheral cathode expansion. The peripheral cathode current collector maintains a stable cell impedance during cell discharge.

40 Claims, 3 Drawing Sheets

ELECTROCHEMICAL CELL

BACKGROUND OF THE INVENTION

This invention relates to an electrochemical cell, a current collector for the cell and a method for cell construction. In particular, the invention relates to a hermetically sealed cell having a reactive cathode and a lithium anode. The electrochemical cell may be used to power body implantable medical devices such as heart pacemakers.

In constructing an electrochemical cell for use in implantable medical devices, a known method of making a cathode pellet is to compress a mixture of powdered metal oxide, a conductive matrix such as graphite or carbon black and a binding material such as polytetrafluroethylene (PTFE). In such a cell, it is essential for uniform discharge of the cell to maintain good contact between the cathode current collector and the cathode material. One known way of providing such contact is to imbed the current collector inside the cathode powder mixture and then compress the mixture into a pellet.

A drawback of imbedding the current collector in the cathode material is that the volume of the cathode typically expands as the cathode is discharged. This expansion of the cathode can cause degradation of the contact between the cathode and the current collector, causing changes in overall cell impedance as the cell is discharged. During latter stages of discharge, contact degradation may cause such an increase in impedance that it causes a significant decrease in cell capacity. Since high reliability in a surgically implanted medical device is essential, an unexpected reduction in cell capacity means that the device must be surgically removed and replaced much earlier than usual.

It should be understood that not all cells with imbedded current collectors will undergo a dramatic impedance increase that requires replacement of the cell. However, even without the problem of early cell replacement, the variability of cell impedance complicates the use of the cell. Powering critical implantable medical devices such as pacemakers, neurostimulators and drug infusing pumps, requires compactness and efficiency of circuit design. If the cells used are too variable in their output, the device would need to be larger and less efficient since the circuits must either increase in complexity to compensate for the output variability or must include capacitors which can provide additional energy storage.

Of course, it is known to provide cathodes without imbedded current collectors. For example, U.S. Pat. No. 3,440,110 issued to Arbter discloses a cathode assembly which includes a support ring into which a cathode material is pressed. This cathode assembly is then pressed into intimate contact with the bottom of the cell housing so that the housing itself can contact the cathode material and act as a current collector. However, in a high reliability electrochemical cell for use in critical medical device applications, reliance on this contact between the cathode and the case can still raise a concern about undesirable impedance variations.

It is, therefore, an object of the present invention to provide an electrochemical cell in which a cathode material which is subject to swelling during discharge has a current collector which will obviate cell impedance variability.

SUMMARY OF THE INVENTION

We have discovered an electrochemical cell having a metal housing and an anode and cathode within the metal housing in which the cathode assembly includes a ring-shaped current collector into which the cathode material is pressed. The cathode is formed into a pellet shape with a flat top surface, a flat bottom surface and a peripheral edge extending between the top and bottom surfaces. The cathode current collector circumferentially surrounds the cathode pellet and is in contact with the peripheral edge of the cathode pellet. Since the cathode is comprised of a material which expands as the cell is discharged, the expansion of the cathode material against the confining ring-shaped current collector will serve as a stable connection between the current collector and the cathode material. The current collector is then electrically connected to the metal housing to allow current flow between the current collector and housing. The housing may therefore be used as one terminal of the cell.

In one aspect of the invention, the cathode current collector can be a ring having an open top portion exposing the top surface of the cathode pellet and an open bottom portion exposing the bottom surface of the cathode pellet. Since neither the top nor bottom portions of the cathode pellet are confined by the current collector, the expansion of the cathode material during discharge may be distributed more evenly on both sides of the ring. Also, another advantage for the open ring shape is that it allows the entire thickness of the cathode assembly to be filled with reactive cathode material to maximize cathode capacity in the cell.

In yet another aspect of the invention, the cathode current collector can have a non-circular shape such as a D-shape in which the ring is reinforced in order to maintain its shape during cathode discharge. The reinforcement can be, for example, a flange extending around the ring or placed selectively at portions of the ring which are susceptible to deformation. Typically, the flange would be provided at the top portion or the bottom portion of the current collector ring. Preferably, the flange extends inwardly around the ring to assist in the retention of the cathode pellet but still exposing the center portion of the cathode pellet.

In yet another aspect of the invention, the metal housing of the cell is provided with an insulator material which electrically separates the cathode material from the metal housing. The ring-shaped current collector then provides the connection to the housing. A connector tab can extend outwardly from the cathode current collector to a location remote from the cathode material where it can be attached to the metal housing by welding or some other means for providing electrical contact.

In yet another aspect of the invention, the ring-shaped current collector allows for construction of the electrochemical cell by a convenient method. The current collector is formed and placed into a circumferentially fitting die where the cathode material can be pressed into a self-supporting pellet which is retained within the cathode current collector. The combined cathode current collector and cathode material can then be placed as a unit into the metal housing of the cell and electrically connected to a portion of the metal housing. Also, a portion of the flange of the current collector ring can be provided with an outward bend to provide a tab to secure the current collector to the metal housing at a portion of the housing that is not insulated. This would also have the effect of making a stable electrical connection between the current collector and the housing. This method is particularly useful when assembling a cell with a pocket-like, D-shaped housing since the current collector assembly can be readily inserted into the pocket of the housing and secured to the housing by welding at the pocket opening.

In yet another aspect of the invention, the cathode current collector allows for the use of an alternative connection to a feedthrough pin which would allow the metal housing of the cell to be used as a negative terminal for the cell (i.e. connecting the anode to the metal housing and the cathode to a feedthrough pin) or for the housing to be neutral with respect to the terminals of the cell (i.e. the anode and cathode each connected to a feedthrough pin).

BRIEF DESCRIPTION OF DRAWINGS

The invention will be further described with reference to the accompanying drawings, in which.

DESCRIPTION OF THE PREFERRED EMBODIMENTS

Figure 1:
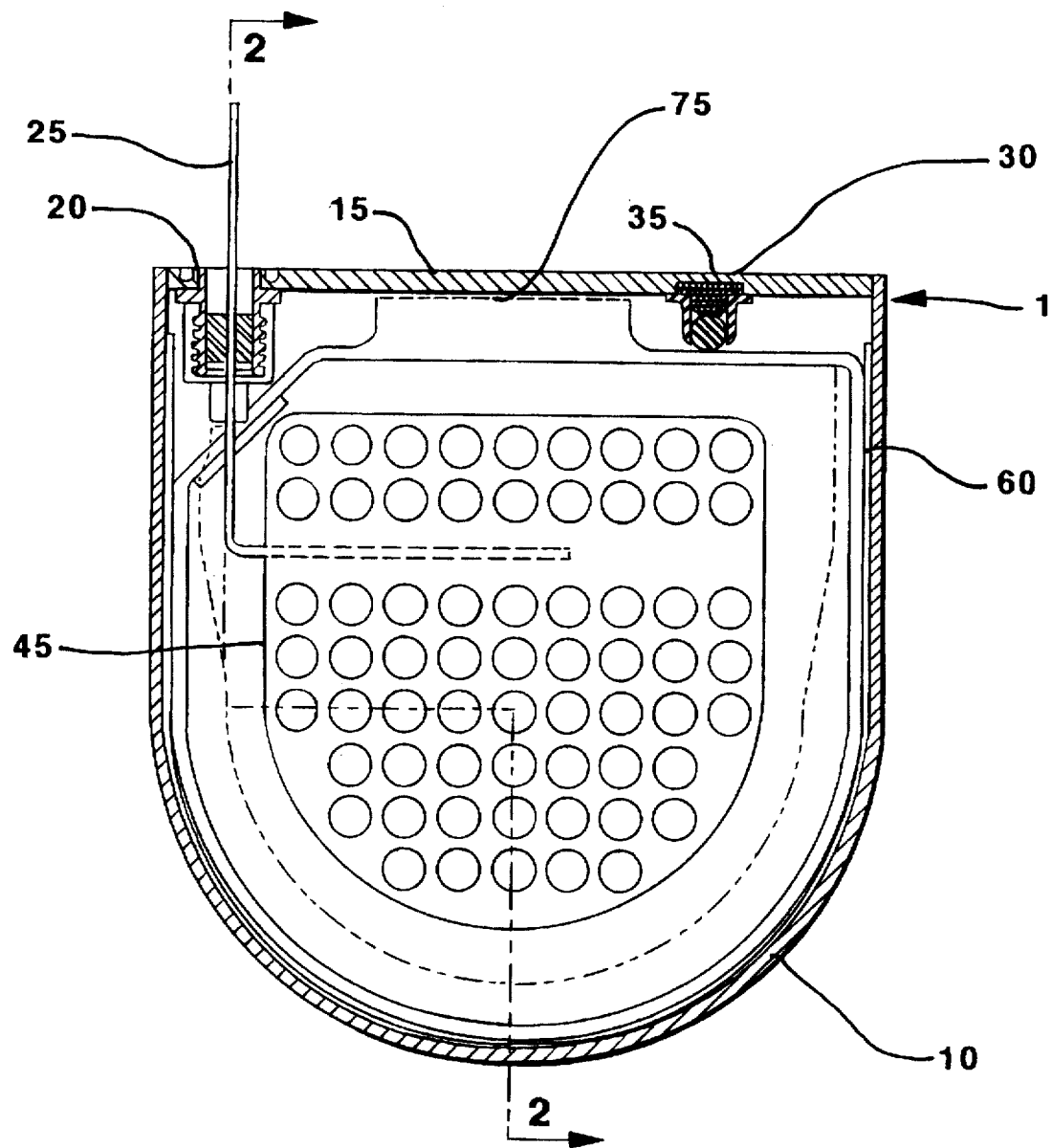
FIG. 1 shows a cross-sectional, elevational view of the cell.

Referring to FIG. 1, a cell 1 according to the invention is shown, including a metal housing in two parts, a D-shaped cell housing body 10 and a housing cover 15, both comprised of a metal such as stainless steel or titanium. The housing cover 15 is placed in the open end of housing body 10 and is hermetically sealed to the housing body 10 with a laser weld around the entire edge of the housing cover 15. The housing cover 15 has an opening 20 to allow a conducting pin 25 to be externalized through a feedthrough with a glass seal 28 which insulates the pin 25 from the housing cover 15 and hermetically seals the opening 20. The housing cover 15 also has a fill port 30 which allows filling of the cell 1 with an electrolyte after the housing cover 15 is welded to the housing body 10. After the cell 1 is charged with a liquid electrolyte, a disc 35 is welded into the fill port 30 to provide a hermetic seal. The liquid electrolyte charged into the cell 1 can include an organic solvent in combination with an ionizing solute. The organic solvent can be, for example, diethyl carbonate, dimethylcarbonate, butylene carbonate, 3-methyl-2-oxazolidone, sulfolane, tetrahydrofuran, methyl-substituted tetrahydrofuran, 1,3-dioxolane, propylene carbonate (PC), ethylene carbonate, gamma -butyrolactone, ethylene glycol sulfite, dimethylsulfite, dimethyl sulfoxide or mixtures thereof and also, for example, low viscosity cosolvents such as tetrahydrofuran (THF), methyl-substituted tetrahydrofuran(Met-THF), dioxolane (DIOX), dimethoxyethane (DME), dimethyl isoxazole (DMI), diethyl carbonate(DEC), ethylene glycol sulfite (EGS), dioxane, dimethyl sulfite (DMS) or the like. The ionizing solute can be a simple or double salt or mixtures thereof, for example, $LiBF_4$, $LiAsF_6$, $LiPF_6$, $LiClO_4$, $LiN(SOCl_2)_3$, or $LiC(SO_2CF_3)_2$, which will produce an ionically conductive solution when dissolved in one or more solvents.

Figure 2:
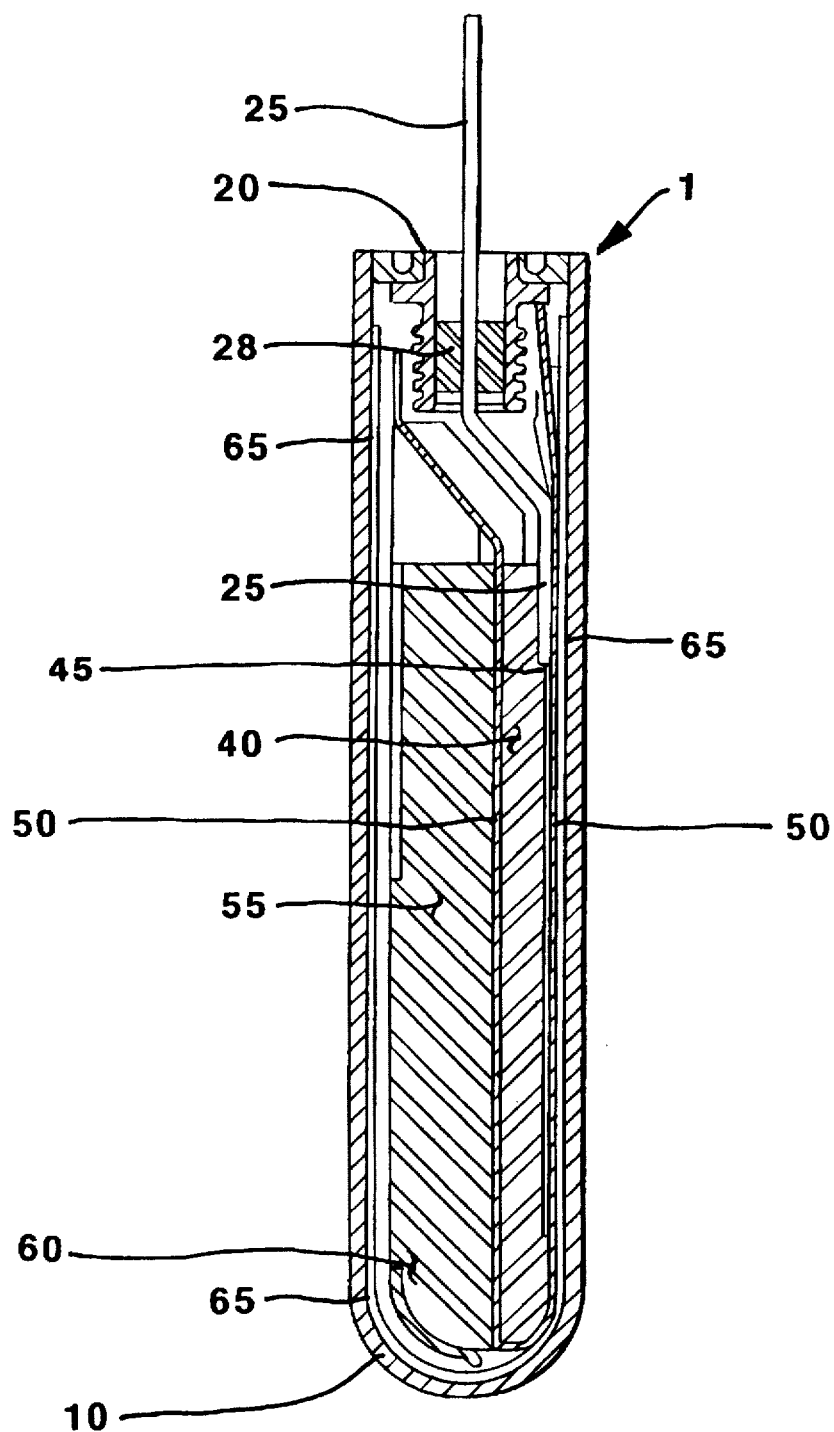
FIG. 2 shows a cross-sectional, side view of the cell along line 2—2 of FIG. 1.

FIG. 2 shows various elements contained within the housing body 10. An anode layer 40 of an active metal is pressed onto a thin anode current collector 45 comprised of a conducting metal such as stainless steel, nickel or titanium. One end of the pin 25 is attached by welding to the anode current collector 45. Active metal anode materials can include, for example, aluminum, the alkali metals, alkaline earth metals and alloys of alkali metals or alkaline earth metals with each other and other metals. The preferred anode materials are lithium, sodium, potassium, calcium and alloys thereof.

A cathode assembly, including a cathode pellet 55 and cathode current collector 60 is spaced apart from the anode layer 40 by separator 50 which is comprised of a porous or a microporous material, preferably polypropylene or polyethylene. The separator 50 completely surrounds and seals the anode 40 and anode current collector 45. Cathode pellet 55 comprises a cathode reactive material which will swell upon discharge. Manganese dioxide is one such material. Other suitable cathode materials could be used instead of manganese dioxide, including vanadium oxide ($V_2O_5$), silver vanadium oxide ($Ag_2V_4O_{11}$) carbon monoflouride, $CoO_2$, $NiO_2$, and $TiS_2$. The cathode pellet 55 may include binders and conductivity enhancers in addition to the reactive cathode material. Binders which may be typically employed in the cathode of the present invention are polytetrafluoroethylene, ethylene/propylene copolymers and the like. Representative of the conductive materials which may be employed as a conductivity enhancer are graphite, carbon and the like. In a cathode pellet 55 having manganese dioxide as the reactive component, binders may comprise between about 1 and about 10 weight percent, preferably between about 1 and about 5 weight percent, of the cathode mix used to make the cathode pellet 55 while the conductive material may comprise between about 1 and about 12 weight percent, preferably between about 3 and about 10 weight percent, of the cathode mix. The solid cathode materials used to make the cathode pellet 55 are in finely divided form so they can be intimately mixed. The cathode mixture may then be pressed into the cathode current collector 60 such that a self supporting cathode pellet 55 is formed within the current collector with peripheral edges of the cathode pellet 55 pressed into intimate contact with the current collector 60. The intimate contact of the current collector 60 around the cathode pellet 55 has the effect of confining the cathode pellet 55 from expanding in diameter as the cathode pellet 55 expands in volume during cell discharge.

A lining material 65, such as polyethylene, electrically insulates the anode 40 and cathode pellet 55 from the interior of the housing body 10. The lining material 65 can be provided in a thin, molded pocket-shaped item or a porous or microporous material which fits closely within the housing body 10. The cathode current collector 60 is electrically connected to the housing body 10 at connector tab 75 which is welded to the housing cover 15.

Figures 3, 4:
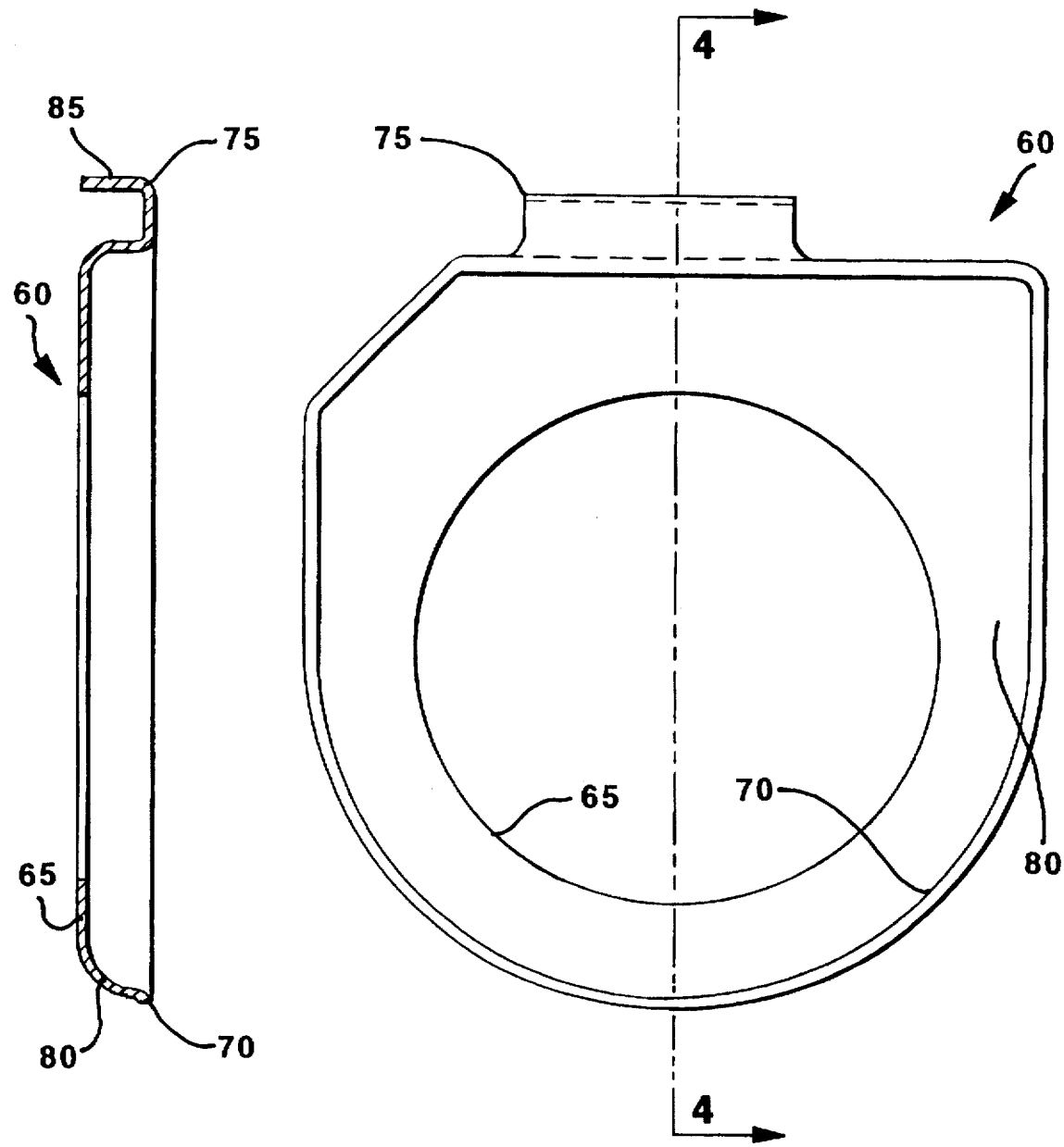
FIG. 3 shows an elevational view of the non-circular ring current collector of FIG. 1.
FIG. 4 shows a cross-sectional view, along line 4—4, of the current collector of FIG. 3.

Referring now to FIG. 3, the cathode current collector 60 has a generally D-shaped outline that is partly semicircular and partly polygonal. The cathode current collector 60 is comprised of a wall 80 with a rim portion 70 and an flange portion 65. The purpose of the flange 65 is to provide a reinforcing means which will retain the shape of the cathode current collector 60 as the cathode pellet expands. Accordingly, the reinforcing means may also include internal or external flanges or a thickened portion of the cathode current collector 60 or other known means for retaining a shape. As in FIG. 3, the current collector 60 preferably has a uniform width, as measured from the rim portion 70 to the inward flange 65.

The cathode current collector 60, comprising an electrically conductive material such as stainless steel or titanium, can be formed by stamping a metal sheet into a cup, cutting excess steel or titanium sheet around the cup but leaving a rectangular tab on a straight edge of the cup. An aperture can then be punched out at the bottom of the cup forming the inward flange 65 portion of the curent collector 60. The rectangular tab can then be bent perpendicularly to create the electrical connector tab 75 of the current collector 60.

After the cathode current collector 60 is formed, a collector-cathode assembly is made. The cathode current collector 60 is placed in a closely fitting die fixture such that the die maintains the shape of the cathode current collector 60 as the collector-cathode assembly is made. A measured amount of cathode mixture comprising powdered manganese dioxide, an inert binding material such as PTFE and conductivity enhancer such as graphite or carbon black is placed into the die inside the current collector. The cathode mixture is compressed in a press within the cathode current collector 60 to form a self-supporting cathode pellet 55 having opposite, flat surfaces exposed. It will be appreciated by those skilled in the art that other active cathode materials which cause the cathode pellet 55 to expand as the cell is discharged could be used in in place of the manganese dioxide. For example, $MnO_2$, $CF_x$, $V_2O_5$, and a silver vanadium oxide (e.g. $Ag_2V_4O_{11}$) could be used alone or in combination as active cathode materials in the present invention.

FIG. 4 provides a cross-sectional view of the cathode current collector 60, including the wall 80 with rim portion 70 and inward flange portion 65. The connector tab 75 has a flat surface 85 which is electrically connected to the housing cover 15.

As an alternative embodiment of the invention, the connector tab 75 on the cathode current collector 60 can be electrically connected to the housing 10 or the cover 15 via a separate, intervening conductor. One end of the conductor may be electrically connected to the housing cover 15. The other end of the conductor is electrically connected to the connector tab 75 of the cathode current collector. The electrical connections can be made by welding.

In yet another embodiment of the invention, a case negative version of the cell (i.e. with the case at the anode potential) can be easily made by connecting the anode current collector 45 to the metal housing cover 15 by a tab similar to the connector tab 75 on the cathode current collector 60 and the anode current collector to the conducting pin 25. Also, a case neutral version of the cell (i.e. with the case at neither the anode or cathode potential) can be made by adding a second conductive pin to the feedthrough or adding a second feedthrough so that each of the current collectors 45, 60 can be connected to a separate conductor pins passing through the metal housing.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive concepts.

We claim:

1. An electrochemical cell comprising:
   (a) a metal housing;
   (b) an anode;
   (c) a cathode in operative relation to the anode, the cathode comprising a material which expands as the cell is discharged, the cathode formed into a pellet shape having a flat top surface, a flat bottom surface and a peripheral edge extending between the top and bottom surfaces;
   (d) a cathode current collector circumferentially surrounding the cathode pellet and in contact with the peripheral edge of the cathode pellet;
   wherein the cathode current collector is a non-circular ring having an open top portion exposing the top surface of the cathode pellet and an open bottom portion exposing the bottom surface of the cathode pellet, and reinforcement means for retaining the non-circular shape of the current collector.

2. An electrochemical cell according to claim 1 wherein said reinforcement means comprises a flange at the top portion or bottom portion of the current collector.

3. An electrochemical cell according to claim 2 wherein the flange is inwardly extending and forming an exposure of a portion of the cathode pellet.

4. An electrochemical cell according to claim 1 further comprising means for electrically connecting the cathode current collector to the metal housing.

5. An electrochemical cell according to claim 4 wherein the means for electrically connecting includes a weld extending between the metal housing and a connector tab extending outwardly from contact with the cathode current collector.

6. An electrochemical cell according to claim 1 wherein the cathode material includes a metal oxide powder as an active cathode material.

7. An electrochemical cell comprising:
   (a) a metal housing;
   (b) an anode;
   (c) a cathode in operative relation to the anode, the cathode comprised of a powder as an active cathode material, the cathode formed into a pellet shape having a flat top surface, a flat bottom surface and a peripheral edge extending between the top and bottom surfaces;
   (d) a cathode current collector circumferentially surrounding said cathode pellet and in contact with the peripheral edge of the cathode pellet, wherein the cathode current collector has an open top portion exposing the top surface of the cathode pellet and an open bottom portion exposing the bottom surface of the cathode pellet;
   (e) an insulator member insulating the metal housing from contact with the cathode pellet; and
   (f) means for electrically connecting the cathode current collector to the metal housing.

8. An electrochemical cell according to claim 7 wherein the cathode current collector includes reinforcement means for maintaining the structural configuration of the cathode current collector.

9. An electrochemical cell according to claim 8 wherein said reinforcement means comprises a flange on the current collector.

10. An electrochemical cell according to claim 9 wherein the flange is inwardly extending and forming an exposure of a portion of the cathode pellet.

11. An electrochemical cell according to claim 7 wherein said means for electrically connecting includes a connector tab extending outward from contact with the cathode current collector.

12. An electrochemical cell according to claim 11 wherein the means for electrically connecting includes a conductor weld extending between the connector tab and the metal housing.

13. A method for constructing an electrochemical cell comprising the steps of:
   (a) forming a metal cathode current collector in a closed ring shape;
   (b) forming a metal housing;
   (c) placing the formed current collector into a circumferentially fitting die;
   (d) placing an amount of a powdered cathode material into the die and current collector;

(e) pressing the cathode material into a self-supporting pellet shape such that the current collector circumferentially surrounds the pellet in a cathode assembly;

(f) placing the cathode assembly into the housing; and (g) electrically connecting the cathode current collector to the metal housing.

14. The method according to claim 13 wherein the metal current collector is formed by the steps of:

(a) stamping a metal sheet into a cup shape; and (b) punching an aperture centrally in said cup shape to leave an upstanding edge and inwardly directed flange.

15. The method according to claim 14 further comprising the step of bending a portion of said upstanding edge outwardly to form a connector tab.

16. The method according to claim 13 further comprising the step of placing an insulator member into the metal housing to insulate the metal housing from contact with the cathode pellet.

17. An electrochemical cell comprising:

(a) a metal housing;

(b) an anode;

(c) a cathode in operative relation to the anode, the cathode comprised of a material which expands as the cell is discharged, the cathode formed into a pellet shape having a flat top surface, a flat bottom surface and a peripheral edge extending between the top and bottom surfaces;

(d) a cathode current collector circumferentially surrounding said cathode pellet and in contact with the peripheral edge of the cathode pellet;

(e) a feedthrough with an insulated, electrically conductive pin extending through a portion of the metal housing; and (f) means for electrically connecting the cathode current collector to the feedthrough pin.

18. An electrochemical cell according to claim 17 wherein the cathode current collector is a non-circular ring having an open top portion exposing the top surface of the cathode pellet and an open bottom portion exposing the bottom surface of the cathode pellet, and reinforcement means for retaining the structural configuration of the current collector.

19. An electrochemical cell according to claim 18 wherein said reinforcement means comprises a flange at the top portion or bottom portion of the current collector.

20. An electrochemical cell according to claim 19 wherein the flange is inwardly extending and forming an exposure of a portion of the cathode pellet.

21. An electrochemical cell according to claim 17 wherein said means for electrically connecting includes a connector tab extending outward from contact with the cathode current collector.

22. An electrochemical cell according to claim 21 wherein the means for electrically connecting includes a weld extending between the connector tab and the feedthrough pin.

23. An electrochemical cell according to claim 17 wherein the cathode material is a powder.

24. An electrochemical cell comprising:

(a) a metal housing;

(b) an anode;

(c) a cathode in operative relation to the anode, the cathode comprised of a powder, the cathode formed into a pellet shape having a flat top surface, a flat bottom surface and a peripheral edge extending between the top and bottom surfaces;

(d) a cathode current collector circumferentially surrounding said cathode pellet and in contact with the peripheral edge of the cathode pellet, wherein the cathode current collector has an open top portion exposing the top surface of the cathode pellet and an open bottom portion exposing the bottom surface of the cathode pellet;

(e) an insulator member insulating the metal housing from contact with the cathode pellet;

(f) a feedthrough with an insulated, electrically conductive pin extending through a portion of the metal housing; and (g) means for electrically connecting the cathode current collector to the feedthrough pin.

25. An electrochemical cell according to claim 24 wherein the cathode current collector includes reinforcement means for maintaining the shape of the cathode current collector.

26. An electrochemical cell according to claim 25 wherein said reinforcement means comprises a flange on the current collector.

27. An electrochemical cell according to claim 26 wherein the flange is inwardly extending and forming an exposure of a portion of the cathode pellet.

28. An electrochemical cell according to claim 24 wherein said means for electrically connecting includes a connector tab extending outward from contact with the cathode current collector.

29. An electrochemical cell according to claim 28 wherein the means for electrically connecting includes a weld extending between the connector tab and the feedthrough pin.

30. A method for constructing an electrochemical cell comprising the steps of:

(a) forming a metal cathode current collector in a closed ring shape;

(b) forming a metal housing having a conductive feedthrough pin extending therethrough;

(c) placing the formed current collector into a circumferentially fitting die;

(d) placing an amount of a powdered cathode material into the die and current collector;

(e) pressing the cathode material into a self-supporting pellet shape such that the current collector circumferentially surrounds the pellet in a cathode assembly;

(f) placing the cathode assembly into the housing; and (g) electrically connecting the cathode current collector to the feedthrough pin.

31. The method according to claim 30 wherein the metal current collector is formed by the steps of:

(a) stamping a metal sheet into a cup shape; and (b) punching an aperture centrally in said cup shape to leave an upstanding edge and inwardly directed flange.

32. The method according to claim 31 further comprising the step of bending a portion of said upstanding edge outwardly to form a connector tab.

33. The method according to claim 30 further comprising the step of placing an insulator member into the metal housing to insulate the metal housing from contact with the cathode pellet.

34. An electrochemical cell, comprising:

(a) a titanium housing;

(b) a lithium anode;

(c) a cathode in operative relation to the anode, the cathode comprising silver vanadium oxide cathode material, the cathode formed into a pellet shape;

(d) a cathode current collector circumferentially surrounding the cathode pellet;

(e) means for electrically connecting the cathode current collector to the titanium housing; and (f) an insulator member insulating the titanium housing from contact with the cathode pellet, wherein the cathode current collector is a non-circular ring having an open top portion exposing the top surface of the cathode pellet and an open bottom portion exposing the bottom surface of the cathode pellet, and reinforcement means for retaining the non-circular shape of the current collector.

35. An electrochemical cell according to claim 34 wherein said reinforcement means comprises a flange at the top portion or bottom portion of the current collector.

36. An electrochemical cell according to claim 35 wherein the flange is inwardly extending and forming an exposure of a portion of the cathode pellet.

37. An electrochemical cell according to claim 34 wherein said means for electrically connecting includes a connector tab extending outward from contact with the cathode current collector.

38. An electrochemical cell according to claim 37 wherein the means for electrically connecting includes a weld extending between the connector tab and the metal housing.

39. An electrochemical cell, comprising:

(a) a metal housing:

(b) an anode;

(c) a cathode in operative relation to the anode, the cathode comprising a material which expands as the cell is discharged, the cathode formed into a pellet shape having a flat top surface, a flat bottom surface and a peripheral edge extending between the top and bottom surfaces;

(d) a cathode current collector circumferentially surrounding the cathode pellet and in contact with the peripheral edge of the cathode pellet; and (e) an insulator member insulating the metal housing from contact with the cathode pellet, wherein the cathode current collector is a non-circular ring having an open top portion exposing the top surface of the cathode pellet and an open bottom portion exposing the bottom surface of the cathode pellet, and reinforcement means for retaining the non-circular shape of the current collector.

40. An electrochemical cell according to claim 39, further comprising means for electrically connecting the cathode current collector to the metal housing.

* * * * *